United States Patent [19]

Hawkins

[11] 4,044,056

[45] Aug. 23, 1977

[54] SYMMETRICAL AROMATIC SULFIDE PRODUCTION

[75] Inventor: Richard T. Hawkins, Orem, Utah

[73] Assignee: Phillips Petroleum Company, Bartlesville, Okla.

[21] Appl. No.: 688,492

[22] Filed: May 20, 1976

[51] Int. Cl.$^2$ ............................................ C07C 148/00
[52] U.S. Cl. ............................. 260/609 E; 260/609 F
[58] Field of Search ...................... 260/609 E, 609 F

[56] References Cited

PUBLICATIONS

Org. Syn., vol. 6, p. 576.

*Primary Examiner*—Delbert R. Phillips

[57] ABSTRACT

Unsymmetrical aromatic sulfides are converted to symmetrical sulfides in a disproportionation reaction by heating, optionally in the presence of a free radical generator and/or oxygen-containing gas, at an elevated temperature and for a period of time sufficient to convert the unsymmetrical sulfides to symmetrical sulfides.

10 Claims, No Drawings

SYMMETRICAL AROMATIC SULFIDE PRODUCTION

This invention relates to the production of symmetrical aromatic sulfides. In accordance with one aspect, this invention relates to the production of symmetrical aromatic sulfides by heating unsymmetrical aromatic sulfides at an elevated temperature and for a period of time sufficient to form symmetrical aromatic sulfides. In accordance with another aspect, this invention relates to a process wherein unsymmetrical aromatic sulfides are heated in the presence of an oxygen-containing gas and/or a free radical generator to produce symmetrical aromatic sulfides.

A wide variety of aromatic sulfides are known, some of which have wide utility. However, the processes currently available for preparing these compounds are so expensive and tedious that the price of these compounds has remained relatively high, thus preventing real commercial development. The present process provides a relatively inexpensive approach to the production of symmetrical aromatic sulfides from unsymmetrical aromatic sulfides whereby unsymmetrical aromatic sulfides are disproportionated to symmetrical aromatic sulfides by heating.

Accordingly, an object of this invention is to provide a process for the production of symmetrical aromatic sulfides.

Another object of this invention is to provide a commercially feasible and relatively inexpensive process for the production of symmetrical aromatic sulfides.

A further object of this invention is to provide a process for the conversion of unsymmetircal aromatic sulfides to commercially usable sulfide products.

Other objects, aspects, and the several advantages of the invention will become apparent to those skilled in the art upon a study of this disclosure and the appended claims.

In accordance with the invention, symmetrical aromatic sulfides are produced by heating at least one unsymmetrical aromatic sulfide at an elevated temperature and for a period of time sufficient to form the symmetrical aromatic sulfides.

More specifically, the present invention relates to a process for the disproportionation of an unsymmetrical aromatic monosulfide to two symmetrical aromatic monosulfides by heating at an elevated temperature and for a period of time sufficient to form the symmetrical sulfides.

In accordance with another embodiment of the invention, heating of unsymmetrical aromatic sulfides to form the symmetrical aromatic sulfides is carried out in the presence of a free radical generator and/or an oxygen-containing gas.

In accordance with one presently preferred embodiment of the invention, unsymmetrical aromatic sulfides which can be employed in the disproportionation process of this invention can be represented by the formula RSR', where R and R' are each selected from the group consisting of aryl and alkaryl radicals having 6 to about 18 carbon atoms, R and R' being different from each other. The symmetrical aromatic sulfides thus produced in the process of this invention can be represented by the formulas RSR and R'SR', where each R and each R' are as defined above, both R radicals being the same and both R' radicals being the same. As used herein, the expression "alkaryl radicals" is meant to include aryl radicals having one or more alkyl substituents.

Examples of some unsymmetrical aromatic sulfides which can be employed in the process of this invention include phenyl 0-tolyl sulfide, phenyl m-tolyl sulfide, phenyl p-tolyl sulfide, phenyl 4-biphenylyl sulfide, phenyl 2-naphthyl sulfide, 4-ethylphenyl 3,5-xylyl sulfide, m-cumenyl 4-butylphenyl sulfide, 2-hexylphenyl 2-methyl-4-octylphenyl sulfide, 4-dodecylphenyl 3-(4-ethyldecyl)phenyl sulfide, phenyl 4-o-terphenylyl sulfide, 2-methyl-1-naphthyl 1-anthryl sulfide, and the like.

Examples of some symmetrical aromatic sulfides which can be produced by the process of this invention include diphenyl sulfide, di-o-tolyl sulfide, di-m-tolyl sulfide, di-p-tolyl sulfide, di-4-biphenylyl sulfide, di-2-naphthyl sulfide, bis(4-ethylphenyl) sulfide, di-3,5-xylyl sulfide, di-m-cumenyl sulfide, bis(4-butylphenyl) sulfide, bis(2-hexylphenyl) sulfide, bis(2-methyl-4-octylphenyl) sulfide, bis(4-dodecylphenyl) sulfide, bis[3-(4-ethyldecyl)phenyl] sulfide, bis(4-o-terphenylyl) sulfide, bis(2-methyl-1-naphthyl) sulfide, di-1-anthryl sulfide, and the like.

Of the various possible symmetrical aromatic sulfides that can be produced by this invention, specific products that have been produced include a mixture of diphenyl sulfide and di-p-tolyl sulfide by the disproportionation of phenyl p-tolyl sulfide and a mixture of diphenyl sulfide and di-4-biphenylyl sulfide by the disproportionation of phenyl 4-biphenylyl sulfide.

Although the temperature at which the disproportionation reaction is conducted can vary over a wide range, depending in part on whether a free radical generator is employed and on whether the reaction is conducted in an atmosphere of a free oxygen-containing gas such as air, the temperature generally will be within the range of about 260° C to about 420° C, preferably about 270° C to about 390° C, a temperature of at least 300° C being used when neither a free radical generator nor a free oxygen-containing gas such as air is employed. The reaction time can very considerably, depending in part on the reaction temperature, but generally will be within the range of about ¼ hour to about 5 days, preferably about 3 hours to about 3 days.

If desired, a free radical generator can be admixed with the unsymmetrical aromatic sulfide to promote the disproportionation reaction. At reaction temperatures less than about 300° C, a free radical generator is required unless an atmosphere of a free oxygen-containing gas such as air is employed. Any free radical source capable of generating a substantial concentration of free radicals at the reaction temperature employed can be used. Examples of some free radical generators which can be employed include disulfides such as diphenyl disulfide and di-1-naphthyl disulfide, sulfur, and organic peroxides, including hydroperoxides, such as αα-dimethylbenzyl hydroperoxide, 1-phenylcyclohexyl hydroperoxide, tert-butyl hydroperoxide, bis(αα-dimethylbenzyl) peroxide, di-tert-amyl peroxide, and the like. Although the amount of free radical generator is not critical, generally, if used, it will be employed in an amount up to about 5 weight percent, preferably in an amount of about 0.3 weight percent to about 3 weight percent, based on the weight of unsymmetrical aromatic sulfide.

The disproportionation of those unsymmetrical aromatic sulfides having no alkyl substituents can be conducted in an atmosphere of a free oxygen-containing gas such as air or in an atmosphere of an inert gas such as nitrogen, helium, or the like. The disproportionation of those unsymmetrical aromatic sulfides having one or more alkyl substituents should be conducted in an atmosphere of an inert gas such as nitrogen, helium, or the like since the presence of a free oxygen-containing gas such as air results in some oxidation of the alkyl substituent(s). The pressure should be sufficient to avoid substantial volatilization of unsymmetrical aromatic sulfide. If desired, when one of the symmetrical aromatic sulfides produced is of lower boiling point than the unsymmetrical aromatic sulfide reactant, the pressure can be maintained sufficiently low to permit volatilization of the more volatile sulfide product as the disproportionation reaction proceeds.

The process of this invention can be conducted batchwise or as a continuous operation. At the completion of the reaction, the aromatic sulfide components in the product mixture can be separated and recovered by conventional techniques such as distillation, extraction, crystallization, gas chromatography, and the like.

The symmetrical aromatic sulfides produced by the process of this invention are useful in various applications, e.g., as high boiling solvents, as heat exchange fluids, as hydraulic fluids, or as intermediates for the production of sulfoxides and sulfones.

EXAMPLES

In each of a series of four runs, phenyl p-tolyl sulfide or phenyl 4-biphenylyl sulfide was heated in a glass flask equipped with thermometer and air condenser, under air or nitrogen at substantially atmospheric pressure. In two of the runs diphenyl disulfide, a free radical generator, was added to the flask. At the end of the reaction period, the reaction mixture was weighed and analyzed by gas chromatography. The reaction conditions, residual reaction product mixture recovery, and concentrations of diphenyl sulfide, phenyl p-tolyl sulfide or phenyl 4-biphenylyl sulfide, and di-p-tolyl sulfide or di-4-biphenylyl sulfide in the residual reaction product mixture are summarized in the following table.

cule to heating at an elevated temperature and for a period of time sufficient to disproportionate said unsymmetrical aromatic sulfide and form symmetrical aromatic sulfides of the formulas RSR and R'SR' wherein each R and each R' are as defined above with both R radicals being the same and both R' radicals being the same, with the proviso that when said heating is carried out at temperatures below about 300° C there are present (1) a free radical source capable of generating a substantial concentration of free radicals at the reaction temperature employed or (2) an atmosphere of a free oxygen-containing gas.

2. A process according to claim 1 wherein said heating is effected at a temperature in the range of about 260° C to about 420° C in the presence of an amount up to about 5 weight percent, based on the weight of unsymmetrical aromatic sulfide, of a free radical generator selected from disulfides, sulfur, and organic peroxides including hydroperoxides.

3. A process according to claim 1 wherein said heating is effected at a temperature in the range of about 260° C to about 420° C in the presence of an oxygen-containing gas.

4. A process according to claim 1 wherein said heating is effected at a temperature of at least 300° C.

5. A process according to claim 1 wherein the unsymmetrical aromatic sulfide is phenyl p-tolyl sulfide and the symmetrical aromatic sulfide product produced is a mixture of diphenyl sulfide and di-p-tolyl sulfide.

6. A process according to claim 5 wherein the heating is effected at a temperature in the range of about 260° C to about 420° C in an inert gas or an oxygen-containing gas and in the presence of an amount up to about 5 weight percent, based on the weight of unsymmetrical aromatic sulfide, of a free radical generator selected from disulfides, sulfur, and organic peroxides including hydroperoxides.

7. A process according to claim 1 wherein the unsymmetrical aromatic sulfide is phenyl 4-biphenylyl sulfide TABLE[a]

| Monosulfide Starting Material | Reaction Conditions | | | | | Analysis of Product | | | | |
|---|---|---|---|---|---|---|---|---|---|---|
| | Atm | Time, hr | Temp., °C | PhSSPh, wt. %[b] | Recovery, wt. %[c] | Mixture, wt. % | | | | |
| | | | | | | PhSPh | PhSTol | PhSB | Tol₂S | B₂S |
| PhSTol[d] | N₂ | 22 | 270–276 | 1.1 | 98.5 | 4 | 93 | — | 2 | — |
| PhSTol[d] | N₂ | 26 | 305–311 | 0.9 | 97.4 | 12 | 73 | — | 15 | — |
| PhSB[e] | Air | 68 | 357–366 | None | 98.2 | 51 | — | 24 | — | 20 |
| PhSB[e] | N₂ | 68 | 357–368 | None | 99.2 | 33 | — | 32 | — | 35 |

[a]Ph = phenyl; Tol = p-tolyl; B = 4-biphenylyl.
[b]Based on weight of monosulfide starting material.
[c]Residual reaction product mixture recovery, expressed as weight percent of the monosulfide starting material plus any diphenyl disulfide employed.
[d]Purity, 98 weight percent; contained 0.8 weight percent p-chlorotoluene and 1.0 weight percent diphenyl sulfide.
[e]Purity, 99 weight percent; contained 1 weight percent 4-bromobiphenyl and no diphenyl sulfide.

Thus, in each of the above runs disproportionation of the unsymmetrical sulfide to the symmetrical sulfides occured, diphenyl sulfide and di-p-tolyl sulfide being produced from phenyl p-tolyl sulfide, and diphenyl sulfide and di-4-biphenylyl sulfide being produced from phenyl 4-biphenylyl sulfide.

I claim:

1. A process for converting unsymmetrical aromatic sulfides to symmetrical aromatic sulfides which comprises subjecting an unsymmetrical aromatic sulfide of the formula RSR' wherein R and R' are different and are each selected from aryl and alkaryl radicals having from 6 to about 18, inclusive, carbon atoms per moleand the symmetrical aromatic sulfide product produced is a mixture of diphenyl sulfide and di-4-biphenylyl sulfide.

8. A process according to claim 7 wherein said heating is carried out at a temperature in the range of about 260° C to about 420° C in the presence of air.

9. A process according to claim 7 wherein said heating is carried out at a temperature in the range of about 300° C to about 420° C in the presence of an inert gas.

10. A process according to claim 1 wherein there is an inert gas present during the disproportionation of unsymmetrical aromatic sulfide having alkyl substituents.

* * * * *